US006274784B1

(12) United States Patent
Bricker et al.

(10) Patent No.: US 6,274,784 B1
(45) Date of Patent: Aug. 14, 2001

(54) PROCESS FOR SEPARATING ALKYLAROMATIC HYDROCARBONS

(75) Inventors: Maureen L. Bricker, Buffalo Grove; Charles P. McGonegal, Addison; Herman A. Zinnen, Evanston, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/430,893

(22) Filed: Nov. 1, 1999

Related U.S. Application Data

(63) Continuation-in-part of application No. 09/175,116, filed on Oct. 19, 1998, now Pat. No. 6,005,153.
(51) Int. Cl.⁷ .................................................... C07C 7/12
(52) U.S. Cl. ........................................... 585/828; 585/831
(58) Field of Search ..................................... 585/828, 831

(56) References Cited

U.S. PATENT DOCUMENTS

| | | | | |
|---|---|---|---|---|
| 3,943,183 | * | 3/1976 | Rosback | 260/674 SA |
| 4,051,192 | * | 9/1977 | Neuzil et al. | 260/674 SA |
| 4,956,522 | * | 9/1990 | Zinnen | 585/828 |

* cited by examiner

*Primary Examiner*—Marian C. Knode
*Assistant Examiner*—Thuan D. Dang
(74) *Attorney, Agent, or Firm*—John C. Tolomei; Frank S. Molinaro; Maryann Maas

(57) ABSTRACT

A process for separating at least one $C_8$ alkylaromatic hydrocarbon from a mixture containing at least one $C_8$ alkylaromatic hydrocarbon and at least one $C_9$ or $C_{10}$ alkylaromatic hydrocarbon using zeolite Y or zeolite Y ion exchanged with a metal selected from the group consisting of calcium, sodium, strontium, a Group IB element, a Group VIII element and mixtures thereof.

2 Claims, 4 Drawing Sheets

US 6,274,784 B1

PROCESS FOR SEPARATING ALKYLAROMATIC HYDROCARBONS

CROSS REFERENCE TO RELATED APPLICATION

This application is a continuation-in-part of our copending application Ser. No. 09/175,116, filed Oct. 19, 1998, now U.S. Pat. No. 6,005,153 all of which is hereby incorporated by reference.

FIELD OF THE INVENTION

The invention is a process for separating $C_8$ alkylaromatic hydrocarbons from $C_9$ and $C_{10}$ alkylaromatic hydrocarbons.

BACKGROUND OF THE INVENTION $C_8$ alkylaromatic hydrocarbons are generally considered to be valuable products, and para-xylene in particular is in high demand. On the other hand, $C_9$ and $C_{10}$ alkylaromatic hydrocarbons are not nearly as valuable but are typically produced as a byproduct in the same aromatic production processes used to produce $C_8$ alkylaromatic hydrocarbons. Various approaches have been used to convert the less valuable $C_9$ and $C_{10}$ alkylaromatic hydrocarbons into $C_8$ alkylaromatic hydrocarbons. One popular approach has been to transalkylate C. and $C_{10}$ alkylaromatic hydrocarbons along with benzene or toluene to form the $C_8$ alkylaromatic hydrocarbons. Specifically, trimethylbenzenes and tetramethylbenzenes have been transalkylated along with benzene and toluene to form xylenes. However, transalkylation reactions are equilibrium limited and the product contains a mixture of unreacted $C_9$ and $C_{10}$ alkylaromatic hydrocarbons along with the desired $C_8$ alkylaromatic hydrocarbons. To increase conversion, commercial processes have utilized a two-stage design with the first stage being a fixed bed reactor and the second stage being a separation unit. Unreacted $C_9$ and $C_{10}$ alkylaromatic hydrocarbons present in the reactor product stream are separated and recycled to the reactor; see for example U.S. Pat. No. 3,211,798.

Once the $C_8$ alkylaromatic hydrocarbons have been produced, they may need to be separated from the unreacted $C_9$ and $C_{10}$ alkylaromatic hydrocarbons. The present invention provides a process for separating the desired $C_8$ alkylaromatic hydrocarbons from the less desired $C_9$ and $C_{10}$ alkylaromatic hydrocarbons using zeolite Y, or ion exchanged zeolite Y as an adsorbent. Zeolite Y has been used as an adsorbent in other applications such as the separation of the specific $C_8$ alkylaromatic hydrocarbon isomers. For example, U.S. Pat. No. 4,255,607 discloses the separation of aromatic $C_8$ isomers by adsorption, preferably contacting the mixture with zeolite Y and then developing the resulting adsorption bond with an ether having selectivity for para-xylene. Japanese Patent No. 79,037,129-B discloses contacting a mixture of $C_8$ aromatic hydrocarbons with a Y-type zeolite containing sodium, calcium, cobalt and or strontium as cation to selectively adsorb meta-xylene. U.S. Pat. No. 4,079,094 discloses separating ethylbenzene from a mixture of xylene isomers by passing through a column of an adsorbent comprising type X or Y zeolite completely exchanged with strontium and potassium. The xylenes are selectively adsorbed and an ethylbenzene stream is withdrawn. U.S. Pat. No. 4,028,428 discloses separating ethylbenzene from a mixture of xylene isomers by contacting the mixture with an adsorbent of a strontiumexchanged type X or type Y zeolite. The xylenes are selectively adsorbed and ethylbenzene may be withdrawn. U.S. Pat. No. 3,998,901 discloses separating ethylbenzene from a mixture of xylene isomers under adsorption conditions with a type X or Y zeolite completely exchanged with strontium and potassium. U.S. Pat. No. 3,997,620 discloses para-xylene being separated from mixtures containing other $C_8$ aromatics by contacting the mixture under adsorption conditions with type X or Y zeolite containing barium and strontium which selectively adsorbs the paraxylene.

The present invention solves a different problem from that of separating $C_8$ alkylaromatic hydrocarbon isomers. Instead, the present invention is directed to at least one $C_8$ alkylaromatic hydrocarbon from at least one $C_9$ or $C_{10}$ alkylaromatic hydrocarbon, which is a problem encountered in processes such as transalkylation.

SUMMARY OF THE INVENTION

The purpose of the invention is to separate at least one $C_8$ alkylaromatic hydrocarbon from at least one $C_9$ or $C_{10}$ alkylaromatic hydrocarbon. The invention involves contacting a mixture containing (I) at least one $C_8$ alkylaromatic hydrocarbon and (II) at least one $C_9$ or $C_{10}$ alkylaromatic hydrocarbon having at least one methyl or ethyl group, or a mixture thereof, with an adsorbent selected from (I) zeolite Y ion exchanged with a metal selected from the group consisting of calcium, sodium, strontium, a Group IB element, a Group VIII element, and mixtures thereof, (II) zeolite Y, and (Ill) combinations thereof to adsorb a $C_8$ alkylaromatic hydrocarbon and a $C_9$ or $C_{10}$ alkylaromatic hydrocarbon. The $C_9$ and/or $C_{10}$ alkylaromatic hydrocarbon(s) are more strongly adsorbed by the adsorbent relative to the $C_8$ alkylaromatic hydrocarbon. The adsorbed $C_8$ alkylaromatic hydrocarbon is desorbed using a desorbent and is collected. The adsorbed $C_9$, $C_{10}$, or mixture of $C_9$ and $C_{10}$ alkylaromatic hydrocarbon(s) is desorbed using the desorbent and collected. In a more specific embodiment of the invention, the desorbent is selected from toluene, benzene, or a mixture thereof.

DETAILED DESCRIPTION OF THE INVENTION

Figure 1:
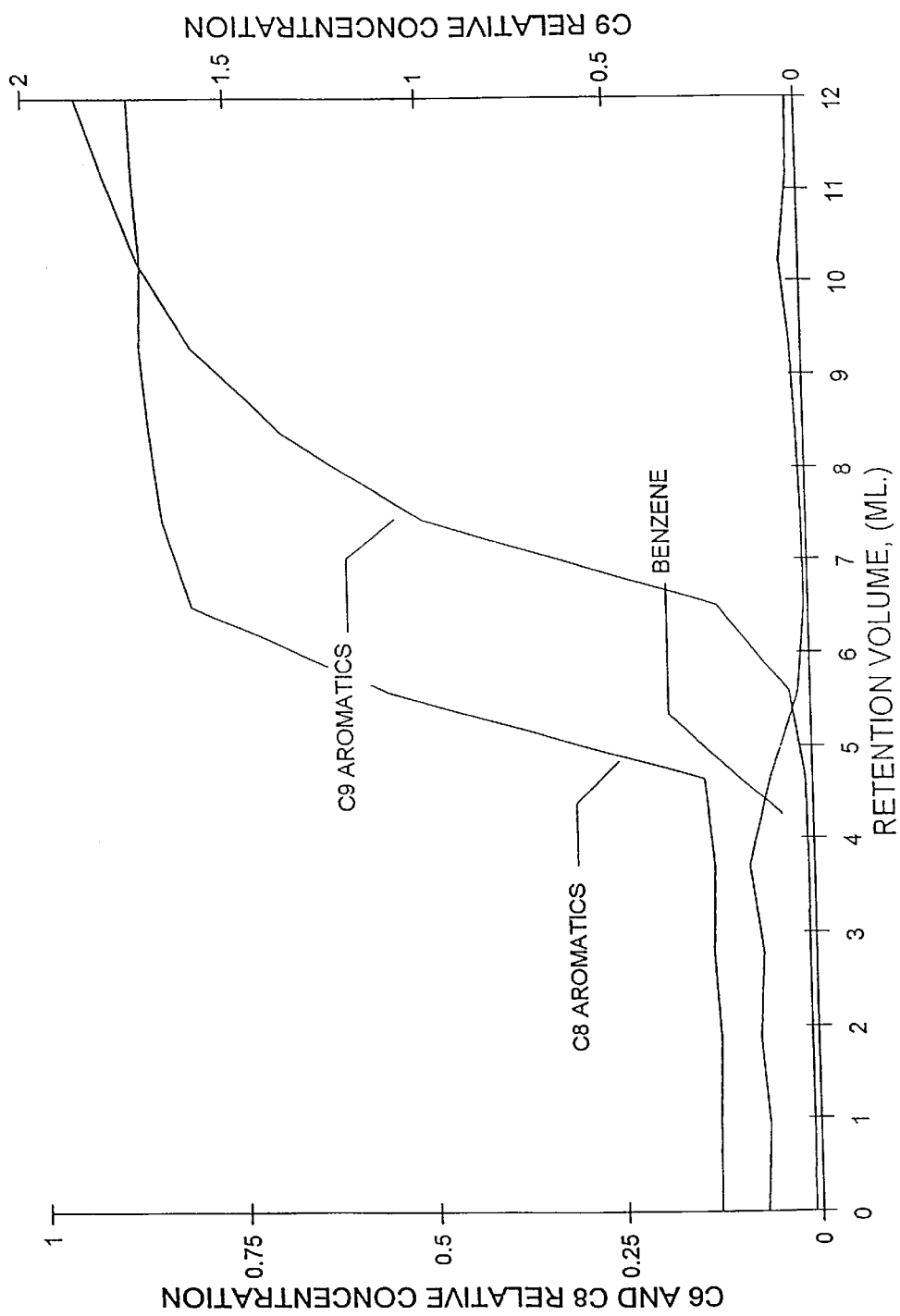
FIG. 1 is the chromatographic plot of the concurrent transalkylation of 1,2,4-trimethylbenzene and separation of the $C_8$ alkylaromatic hydrocarbon products using dealuminated Y zeolite as both the catalyst and adsorbent as described in Example 1. The $C_8$ alkylaromatic hydrocarbons are summed and the sum of the concentrations is plotted. Similarly, the $C_9$ alkylaromatic hydrocarbons are summed and the sum of the concentrations is plotted.

In general terms, the invention involves using an adsorbent in a separation process to separate at least one $C_8$ alkylaromatic hydrocarbon from at least one $C_9$ or $C_{10}$ alkylaromatic hydrocarbon. The mixture to be separated contains (I) at least one $C_5$ alkylaromatic hydrocarbon and (II) at least one $C_9$ or $C_{10}$ alkylaromatic hydrocarbon having at least one methyl or ethyl group, or a mixture thereof. The mixture is contacted with specific adsorbents chosen to have preferential selectivity for the $C_9$ or $C_{10}$ alkylaromatic hydrocarbons, described in detail below, to adsorb the $C_9$ or $C_{10}$ alkylaromatic hydrocarbons relative to the $C_8$ alkylaromatic hydrocarbons. The $C_8$ alkylaromatic hydrocarbons are carried with the fluid flow, removed from the system, and collected. A desorbent is used to desorb the $C_9$ or $C_{10}$ alkylaromatic hydrocarbons which are removed from the system and collected.

The specific adsorbents of the invention were discovered to have a selectivity for $C_9$ and $C_{10}$ alkylaromatic hydrocarbon reactants relative to that of $C_8$ alkylaromatic hydrocarbons. In other words, the adsorbent was discovered to be capable of preferentally adsorbing $C_9$ and $C_{10}$ alkylaromatic hydrocarbons relative to $C_8$ alkylaromatic hydrocarbons at the operating conditions of the invention. Specifically, the adsorbent used in the present invention is zeolite Y including dealuminated zeolite Y having a $SiO_2/Al_2O_3$ ratio in the range of from about 5 to about 25, and preferably from about 6 to about 12. The zeolite Y may be ion exchanged withfcalcium, sodium, strontium, a Group IB element, a Group VIII element, or mixtures thereof and used successfully in the present invention. The structure of zeolite Y is described, and further references are provided, in Meier, W. M.; Olson, D. H.; Baerlocher, Ch. *Atlas of Zeolite Structure Types*, 4*th* Edition, Elsevier: Boston, 1996, pp. 6263 and 104–105. See also U.S. Pat. No. 4,940,830 which is incorporated by reference. A preferred adsorbent is zeolite Y ion exchanged with sodium, and a most preferred adsorbent is zeolite Y-54 ion exchanged with sodium and strontium; see Example 3. Two or more adsorbents may be used together.

Particular adsorbents may retain the individual isomers of $C_8$ alkylaromatic hydrocarbons differently, which may be advantageous in specific applications. For example, zeolite Y ion exchanged with sodium has a greater selectivity for meta-xylene as compared to para-xylene and ortho-xylene; see Example 2. Therefore, a product stream may be withdrawn that is depleted in meta-xylene as compared to an equilibrium mixture of all C. alkylaromatic hydrocarbon isomers.

The adsorbent is preferably used in a fixed bed mode at operating conditions of a temperature ranging from about 75° C. to about 300° C. and pressures from atmospheric to about 600 psig. The operating conditions should be chosen so that all components are in the same phase, gas or liquid. The gas phase allows higher mass transfer while the liquid phase provides higher adsorbent loading.

The desorbent must be capable of desorbing the $C_9$ and $C_{10}$ alkylaromatic hydrocarbon reactants. Examples of acceptable desorbents include benzene and toluene and a mixture thereof. The mixture to be separated contains at least one $C_9$ or $C_{10}$ alkylaromatic hydrocarbon preferably containing at least one methyl or ethyl group. Preferred $C_9$ and $C_{10}$ alkylaromatic hydrocarbons are trimethylbenzenes andI tetramethylbenzenes and examples of specific suitable alkylaromatic hydrocarbons include, but are not limited to, toluene, 1,3,5-trimethylbenzene, 1,2,4-trimethylbenzenre, 1,2,3-trimethylbenzene, and the tetramethylbenzene isomers. Other alkylaromatic hydrocarbons such as methylethylbenzenes and propylbenzenes may also be present in the mixture. The mixture to be separated should not contain components that would significantly alter the capacities or selectivities of the adsorbent or desorbent. The product stream withdrawn from the simulated moving bed will contain desorbent and the desired $C_8$ alkylaromatic hydrocarbon products which are usually ortho- meta- and para-xylenes. The product stream may be purified using techniques such as distillation or crystallization.

The examples are directed to systems containing both the adsorbents described herein and a transalkylation catalyst. The $C_8$ alkylaromatic hydrocarbons are produced within the system from transalkylation of the $C_9$ or $C_{10}$ alkylaromatic hydrocarbons with benzene or toluene or a mixture thereof. Then, the $C_8$ alkylaromatic hydrocarbons are separated from the $C_9$ or $C_{10}$ alkylaromatic hydrocarbons through contact with the adsorbent that selectively adsorbs the $C_9$ or $C_{10}$ alkylaromatic hydrocarbons. The $C_8$ alkylaromatic hydrocarbons are collected. A desorbent is used to desorb the $C_9$ or $C_{10}$ alkylaromatic hydrocarbons which are then collected.

EXAMPLE 1

A 70 mL column was loaded with 34.9 grams of a single 2040 mesh compound which is capable of functioning both as a catalyst and as an adsorbent, dealuminated zeolite Y having a $SiO_2/Al_2O_3$ ratio of 6. The column was placed in a heated enclosure at 250° C. and maintained at process pressure of 28 psig using back pressure regulators. Toluene desorbent and hydrogen were directed into the columns at measured rates. A 20 mL pulse of 1,2,4-trimethylbenzene feed was introduced and the desorbent flow was resumed. The effluent of the system was condensed and analyzed by gas chromatography to obtain the composition of the effluent. FIG. 1 shows the concentration profiles of the effluent beginning with the background level of toluene desorbent and $C_8$ alkylaromatic hydrocarbons, the background level of $C_8$ alkylaromatic hydrocarbons is due to toluene disproportionation. The concentrations of each individual species in a carbon number class were summed and the sum of the concentrations plotted. A region of effluent enriched in $C_8$ alkylaromatic hydrocarbons elutes prior to a region enriched in $C_9$ alkylaromatic hydrocarbons showing that the separation of $C_8$ alkylaromatic hydrocarbons from the $C_9$ alkylaromatic hydrocarbons is occurring.

EXAMPLE 2

Figure 2:
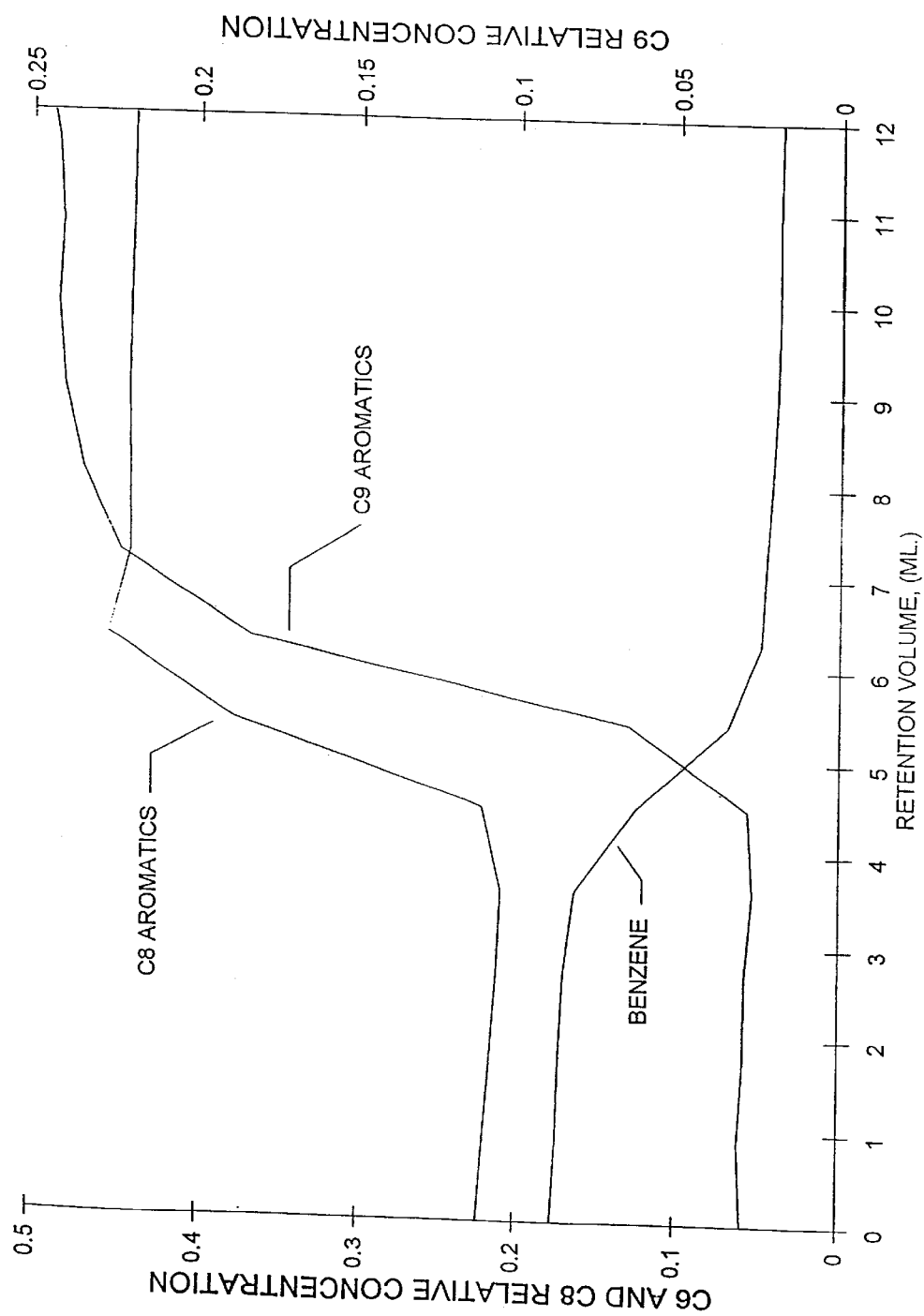
FIG. 2 is the chromatographic plot of the concurrent transalkylation of 1,3,5-trimethylbenzene and separation of the $C_8$ alkylaromatic hydrocarbon products using a homogeneous mixture of H-mordenite bound with alumina catalyst and Na-Y zeolite bound with clay adsorbent as described in Example 2. The $C_8$ alkylaromatic hydrocarbons are summed and the sum of the concentrations is plotted. Similarly, the $C_9$ alkylaromatic hydrocarbons are summed and the sum of the concentrations is plotted.

A 70 mL column was loaded with a homogeneous mixture of 2040 mesh catalyst and adsorbent. The catalyst was H-mordenite bound with alumina (12.75 grams) and the adsorbent was Na-Y zeolite bound with clay (24.75 grams). The column was placed in a heated enclosure at 250° C. and maintained at process pressure of 62 psig using back pressure regulators. Toluene desorbent and hydrogen were directed into the columns at measured rates. A 20 mL pulse of a feed containing 50 mass percent toluene and 50 mass percent 1,3,5-rimethylbenzene was introduced and the desorbent flow was resumed. The effluent of the system was condensed and analyzed by gas chromatography to obtain the composition of the effluent. FIG. 2 shows the concentration profiles of the effluent beginning with the background level of toluene desorbent and $C_8$ alkylaromatic hydrocarbons; the background level of $C_8$ alkylaromatic hydrocarbons is due to toluene disproportionation. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that separation is occurring.

EXAMPLE 3

57 Grams of Na-Y-54 adsorbent containing 10.42 weight percent aluminum (volatile free) and 6.92 weight percent sodium (volatile free) were loaded into a column. 92 Grams of $SrCl_2.H_2O$ were dissolved in 3 liters of water and the resultant solution was circulated through the column for 20 hours at 70° C. and ambient pressure. The solution was drained from the column and the adsorbent rinsed with 5 L of water. The adsorbent was unloaded from the column and dried in a drying oven for about 16 hours in air at 90° C. The dried adsorbent was analyzed using an inductively coupled argon plasma atomic emission spectrophotometer to have 9.03 weight percent aluminum, 1.77 weight percent sodium, and 4.36 weight percent strontium, all on a volatile-free basis.

Figure 3:
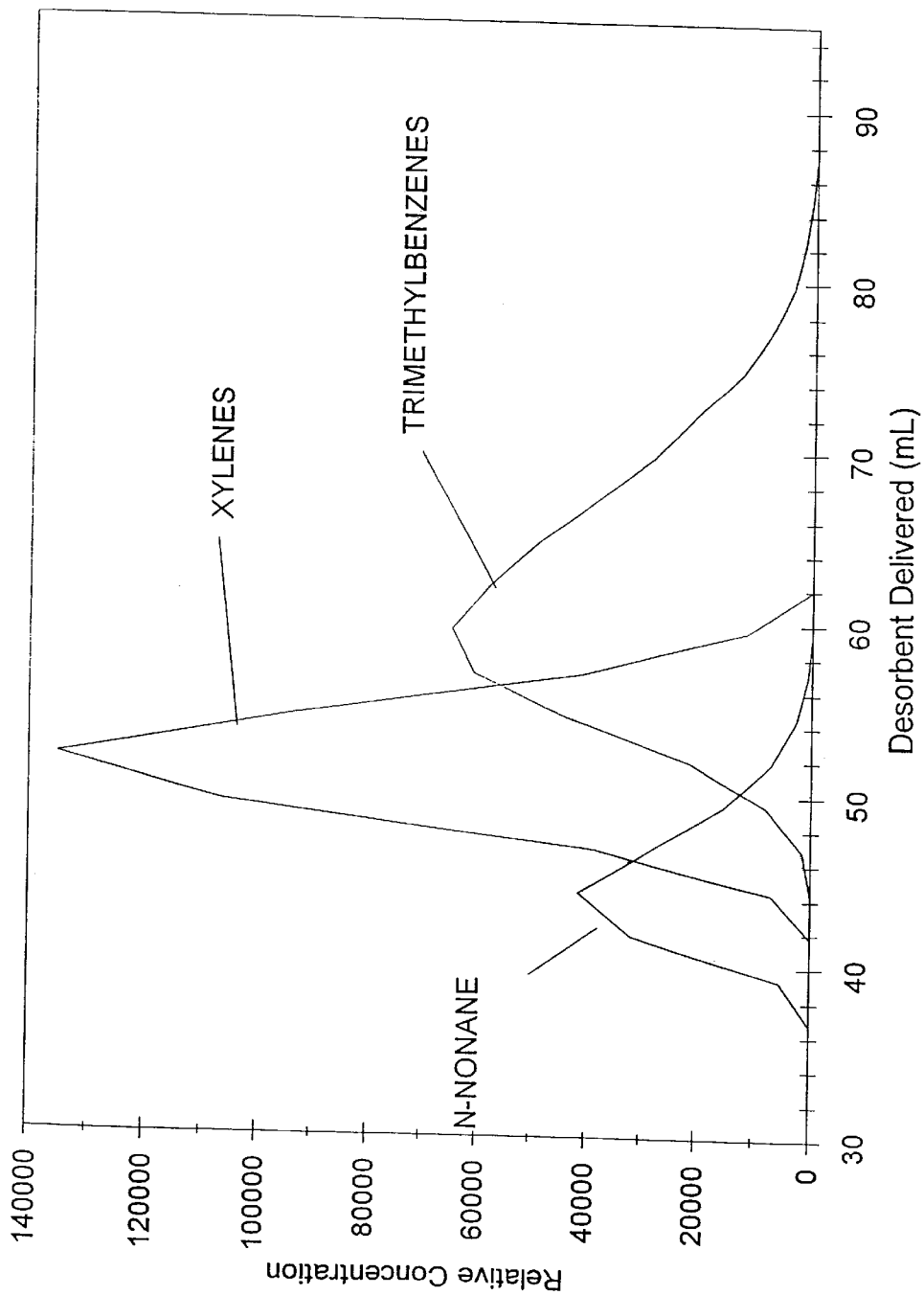
FIG. 3 is the chromatographic plot of the liquid phase separation of the $C_8$ alkylaromatic hydrocarbons from $C_9$ alkylaromatic hydrocarbons using a Na-Y zeolite ion exchanged with strontium adsorbent as described in Example 3. The $C_8$ alkylaromatic hydrocarbons are summed and the sum of the concentrations is plotted. Similarly, the $C_9$ alkylaromatic hydrocarbons are summed and the sum of the concentrations is plotted.

The column containing the dried adsorbent was placed in a heated enclosure at 150° C. and maintained at a pressure of 70 psig using back pressure regulators. Liquid phase toluene desorbent was directed into the columns at measured rates. A liquid phase 2 mL pulse of a feed containing equal parts normal nonane, ethylbenzene, para-xylene, meta-xylene, ortho-xylene, para-methylethylbenzene, meta-methylethylbenzene, ortho-methylethylbenzene, 1,2,3-trimethylbenzene, 1,2,4-trimethylbenzene and 1,3,5-trimethylbenzene was introduced and the desorbent flow was resumed. While in the column, the $C_8$ alkylaromatic hydrocarbons and $C_9$ alkylaromatic hydrocarbons were maintained in the liquid phase. The effluent of the system was analyzed by gas chromatography to obtain the composition of the effluent. FIG. 3 shows the concentration profiles of the effluent beginning with the background level of toluene desorbent. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that separation of the $C_8$ alkylaromatic hydrocarbons from the $C_9$ alkylaromatic hydrocarbons is occurring.

Figure 4:
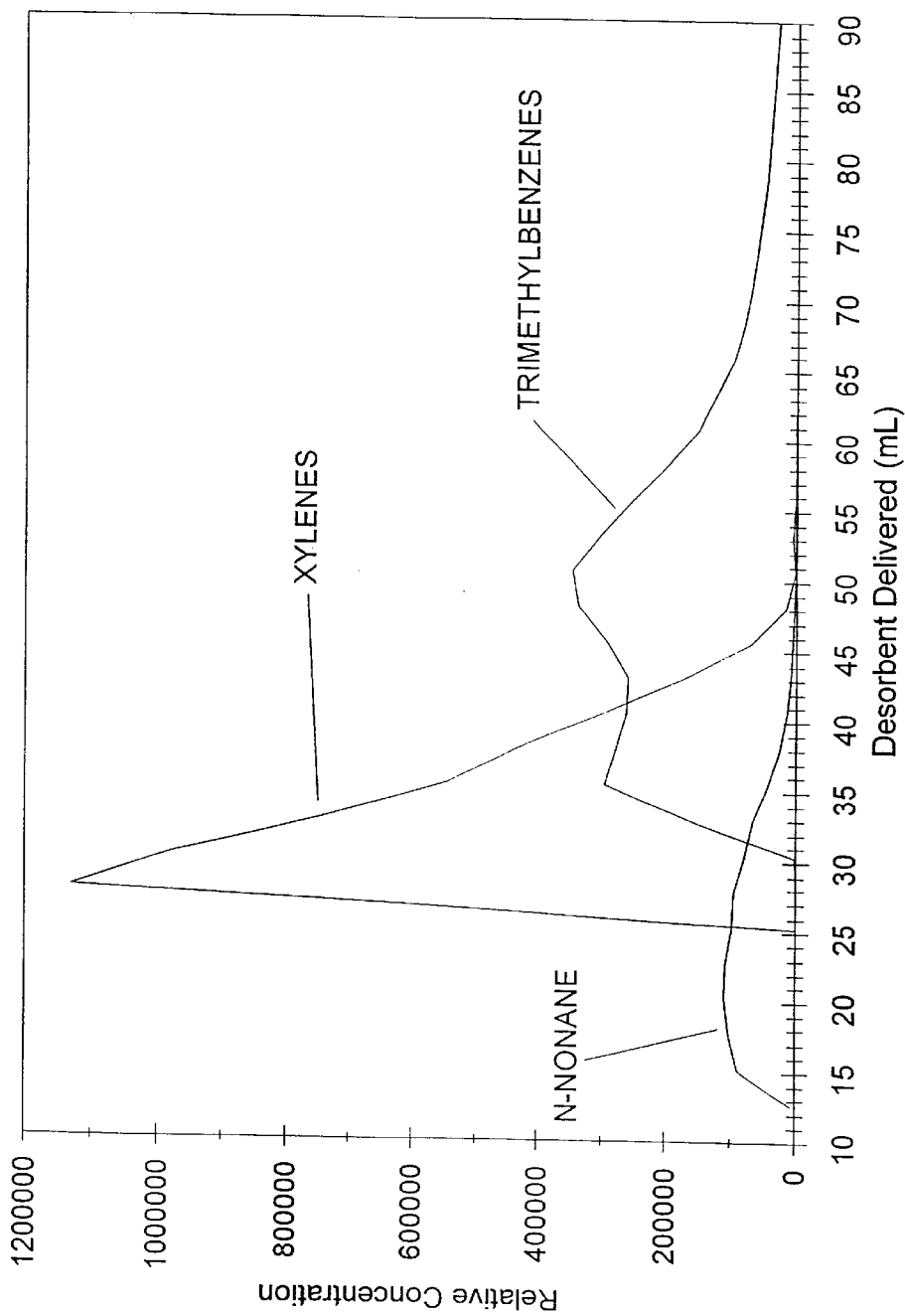
FIG. 4 is the chromatographic plot of the vapor phase separation of the $C_8$ alkylaromatic hydrocarbons from $C_9$ alkylaromatic hydrocarbons using a Na-Y zeolite ion exchanged with strontium adsorbent as described in Example 3. The $C_8$ alkylaromatic hydrocarbons are summed and the sum of the concentrations is plotted. Similarly, the $C_9$ alkylaromatic hydrocarbons are summed and the sum of the concentrations is plotted.

The pulse test was repeated with the components being maintained in the vapor phase. The column containing the dried adsorbent was again placed in a heated enclosure at 150° C. and maintained at a pressure of 10 psig using back pressure regulators. Toluene desorbent was directed into the columns at measured rates. A 20 mL pulse of a feed containing 32 mass percent toluene, 9.7 mass percent para-xylene, 14.8 mass percent meta-xylene, 9.4 mass percent ortho-xylene, 9.7 mass percent 1,3,5-trimethylbenzene, 20.0 mass percent 1,2,4-trimethylbenzene, and 4 mass percent 1,2,5-trimethylbenzene was introduced and the desorbent flow was resumed. While in the column, the $C_8$ alkylaromatic hydrocarbons and $C_9$ alkylaromatic hydrocarbons were maintained in the vapor phase. The effluent of the system was condensed and analyzed by gas chromatography to obtain the composition of the effluent. FIG. 4 shows the concentration profiles of the effluent beginning with the background level of toluene desorbent and $C_8$ alkylaromatic hydrocarbons; the background level of $C_8$ alkylaromatic hydrocarbons is due to toluene disproportionation. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that separation of the $C_8$ alkylaromatic hydrocarbons from the $C_9$ alkylaromatic hydrocarbons is occurring.

What is claimed is:

1. A separation process comprising:
    a) contacting a mixture containing (I) at least one $C_8$ alkylaromatic hydrocarbon and (II) at least one $C_9$ or $C_{10}$ alkylaromatic hydrocarbon having at least one methyl or ethyl group, or a mixture thereof, with an adsorbent selected from the group consisting of zeolite Y ion exchanged with a metal selected from the group consisting of calcium, strontium, a Group IB element, a Group VIII element and mixtures thereof, and combinations thereof to selectively adsorb the $C_9$ or $C_{10}$ alkylaromatic hydrocarbon;
    b) collecting the $C_8$ alkylaromatic hydrocarbon; and
    c) desorbing the adsorbed $C_9$, $C_{10}$, or mixture of $C_9$ and $C_{10}$, alkylaromatic hydrocarbon(s) using a desorbent and collecting the $C_9$, $C_{10}$, or mixture of $C_9$ and $C_{10}$ alkylammatic hydrocarbon(s).

2. The process of claim 1 wherein the desorbent is selected from the group consisting of toluene, benzene, and a mixture thereof.

* * * * *